(12) United States Patent
Allen et al.

(10) Patent No.: US 10,155,944 B2
(45) Date of Patent: Dec. 18, 2018

(54) TAILED PRIMER FOR CLONED PRODUCTS USED IN LIBRARY CONSTRUCTION

(71) Applicant: Integrated DNA Technologies, Inc., Skokie, IL (US)

(72) Inventors: Shawn Allen, Williamsburg, IA (US); Adam Clore, Iowa City, IA (US)

(73) Assignee: Integrated DNA Technologies, Inc., Coralville, IA (US)

( * ) Notice: Subject to any disclaimer, the term of this patent is extended or adjusted under 35 U.S.C. 154(b) by 363 days.

(21) Appl. No.: 15/228,281

(22) Filed: Aug. 4, 2016

(65) Prior Publication Data

US 2017/0037395 A1    Feb. 9, 2017

Related U.S. Application Data

(60) Provisional application No. 62/201,408, filed on Aug. 5, 2015.

(51) Int. Cl.
*C12N 15/10* (2006.01)

(52) U.S. Cl.
CPC ....... *C12N 15/1093* (2013.01); *C12N 15/102* (2013.01)

(58) Field of Classification Search
None
See application file for complete search history.

(56) References Cited

U.S. PATENT DOCUMENTS

| | | | |
|---|---|---|---|
| 6,040,439 | A | 3/2000 | Hayakawa et al. |
| 7,691,316 | B2 | 4/2010 | Ngo et al. |
| 2010/0216648 | A1 | 8/2010 | Staehler et al. |
| 2011/0172127 | A1 | 7/2011 | Jacobson et al. |

FOREIGN PATENT DOCUMENTS

WO    WO-2005054492 A1 *    6/2005    ........... C12N 15/102

OTHER PUBLICATIONS

Janiak-Spens et al. (2000) "Functional roles of conserved amino acid residues surrounding the phosphorylatable histidine of the yeast phosphorelay protein YPD1" Molecular Microbiology 37(1):136-144.*
Caruthers et al., "Chemical synthesis of deoxyoligonucleotides by the phosphoramidite method" Methods in Enzymology (1987) 154:287-313.
Tian et al., "Advancing high-throughput gene synthesis technology" Mol. BioSyst (2009) 5, 714-722.
Gao, X. et al., "Thermodynamically balanced inside-out (TBIO) PCR-based gene synthesis: a novel method of primer design for high-fidelity assembly of longer gene sequences" Nucleic Acids Research (2003) 31(22):e143.
Sierzchala, A.B. et al., "Solid-Phase Oligodeoxynucleotide Synthesis: A Two-Step Cycle Using Peroxy Anion Deprotection" JACS (2003) 125:13427-13441.
Azhayev, A.V. et al., "Amide group assisted 3'-dephosphorylation of oligonucleotides synthesized on universal A-supports" Tetrahedron (2001) 57:4977-4986.

(Continued)

*Primary Examiner* — Karen S. Weiler
(74) *Attorney, Agent, or Firm* — John A. Petravich

(57) ABSTRACT

This invention pertains to improved methods for the synthesis of long, double stranded nucleic acid sequences containing difficult to clone or variable regions.

1 Claim, 2 Drawing Sheets

(56) References Cited

OTHER PUBLICATIONS

Kozlov, I.A. et al., "Significant improvement of quality for long oligonucleotides by using controlled pore glass with large pores" Nucleosides, Nucleotides and Nucleic Acids (2005) 24(5-7):1037-1041.
Czar, M.J. et al., "Gene synthesis demystified" Trends in Biotechnology (2008) 27(2):63-72.
Damha, M.J. et al., "An improved procedure for derivatization of controlled-pore glass beads for solid-phase oligonucleotide synthesis" Nucleic Acids Research (1990) 18(13):3813-3821.
Bang, D. et al. "Gene synthesis by circular assembly amplification" Nature Methods (2008) 5:37-39.
Carr, P.A. et al., "Protein-mediated error correction for de novo DNA synthesis" Nucleic Acids Research (2004) 32, e162.
Gibson, D.G. et al., "Complete Chemical Synthesis, Assembly, and Cloning of a Mycoplasma genitalium Genome" Science (2008) 319:1215-1220.
Kodumal, S.J. et al., "Total synthesis of long DNA sequences: Synthesis of a contiguous 32-kb polyketide synthase gene cluster" PNAS (2004) 101(44):15573-15578.
Villalobos, A. et al., "Gene Designer: a synthetic biology tool for constructing artificial DNA segments" BMC Bioinformatics (2006) 7:285.
Larionov, V. et al., "Specific cloning of human DNA as yeast artificial chromosomes by transformation-associated recombination" PNAS (1996) 93:491-496.

\* cited by examiner

TAILED PRIMER FOR CLONED PRODUCTS USED IN LIBRARY CONSTRUCTION

FIELD OF THE INVENTION

This invention pertains to improved methods for the preparation of long, double stranded nucleic acid sequences containing regions of low complexity, repeating elements, difficult to assemble and clone elements, or variable regions containing mixed bases.

BACKGROUND OF THE INVENTION

Synthetic DNA sequences are a vital tool in molecular biology. They are used in gene therapy, vaccines, DNA libraries, environmental engineering, diagnostics, tissue engineering and research into genetic variants. Long artificially-made nucleic acid sequences are commonly referred to as synthetic genes; however the artificial elements produced do not have to encode for genes, but, for example, can be regulatory or structural elements. Regardless of functional usage, long artificially-assembled nucleic acids can be referred to herein as synthetic genes and the process of manufacturing these species can be referred to as gene synthesis. Gene synthesis provides an advantageous alternative from obtaining genetic elements through traditional means, such as isolation from a genomic DNA library, isolation from a cDNA library, or PCR cloning. Traditional cloning requires availability of a suitable library constructed from isolated natural nucleic acids wherein the abundance of the gene element of interest is at a level that assures a successful isolation and recovery.

Artificial gene synthesis can also provide a DNA sequence that is codon optimized. Given codon redundancy, many different DNA sequences can encode the same amino acid sequence. Codon preferences differ between organisms and a gene sequence that is expressed well in one organism might be expressed poorly or not at all when introduced into a different organism. The efficiency of expression can be adjusted by changing the nucleotide sequence so that the element is well expressed in whatever organism is desired, e.g., it is adjusted for the codon bias of that organism. Widespread changes of this kind are easily made using gene synthesis methods but are not feasible using site-directed mutagenesis or other methods which introduce alterations into naturally isolated nucleic acids.

As another example, a synthetic gene can have restriction sites removed and new sites added. As yet another example, a synthetic gene can have novel regulatory elements or processing signals included which are not present in the native gene. Many other examples of the utility of gene synthesis are well known to those with skill in the art.

Furthermore, a sequence isolated from genomic DNA or cDNA libraries only provides an isolate having that nucleic acid sequence as it exists in nature. It is often desirable to introduce alterations into that sequence. For example a randomized mutant library can be created wherein random bases are inserted into desired positions and then expressed to find desirable properties relative to the wild type sequence. This approach does not allow for specific placement of degenerate bases. In another example, a gene enriched with repeat sequences could be used for genomic mapping or marking.

Although the cost of synthesizing a large library of genes can be substantial, the ability to optimize or change the characteristics of the encoded enzyme or antibody can result in a powerful biological tool or therapeutic. Recombinant antibodies such as Humira® (Abbot Laboratories, Inc.) are widely used as therapeutics, and many others are used as research tools. Those in the art also appreciate that many commercial proteins, such as enzymes, originated from mutant libraries.

Gene synthesis employs synthetic oligonucleotides as the primary building block. Oligonucleotides are made using chemical synthesis, most commonly using betacyanoethyl phosphoramidite methods, which are well-known to those with skill in the art (M. H. Caruthers, Methods in Enzymology 154, 287-313 (1987)). Using a four-step process, phosphoramidite monomers are added in a 3' to 5' direction to form an oligonucleotide chain. During each cycle of monomer addition, a small amount of oligonucleotides will fail to couple (n−1 product). Therefore, with each subsequent monomer addition the cumulative population of failures grows. Also, as the oligonucleotide grows longer, the base addition chemistry becomes less efficient, presumably due to steric issues with chain folding. Typically, oligonucleotide synthesis proceeds with a base coupling efficiency of around 99.0 to 99.2%. A 20 base long oligonucleotide requires 19 base coupling steps. Thus assuming a 99% coupling efficiency, a 20 base oligonucleotide should have $0.99^{19}$ purity, meaning approximately 82% of the final end product will be full length and 18% will be truncated failure products. A 40 base oligonucleotide should have $0.99^{39}$ purity, meaning approximately 68% of the final end product will be full length and 32% will be truncated failure products. A 100 base oligonucleotide should have $0.99^{99}$ purity, meaning approximately 37% of the final product will be full length and 63% will be truncated failure products. In contrast, if the efficiency of base coupling is increased to 99.5%, then a 100 base oligonucleotide should have a $0.995^{99}$ purity, meaning approximately 61% of the final product will be full length and 39% will be truncated failure products.

Using gene synthesis methods, a series of synthetic oligonucleotides are assembled into a longer synthetic nucleic acid, e.g. a synthetic gene. The use of synthetic oligonucleotide building blocks in gene synthesis methods with a high percentage of failure products present will decrease the quality of the final product, requiring implementation of costly and time-consuming error correction methods. For this reason, relatively short synthetic oligonucleotides in the 40-60 base length range have typically been employed in gene synthesis methods, even though longer oligonucleotides could have significant benefits in assembly. It is well appreciated by those with skill in the art that use of high quality synthetic oligonucleotides, e.g. oligonucleotides with few error or missing bases, will result in high quality assembly of synthetic genes than the use of lower quality synthetic oligonucleotides.

Some common forms of gene assembly are ligation-based assembly, PCR-driven assembly (see Tian et al., Mol. Biosyst., 5, 714-722 (2009)) and thermodynamically balanced inside-out based PCR (TBIO) (see Gao X. et al., *Nucleic Acids Res.* 31, e143). All three methods combine multiple shorter oligonucleotides into a single longer end-product.

Therefore, to make genes that are typically 500 to many thousands of bases long, a large number of smaller oligonucleotides are synthesized and combined through ligation, overlapping, etc., after synthesis. Typically, gene synthesis methods only function well when combining a limited number of synthetic oligonucleotide building blocks and very large genes must be constructed from smaller subunits using iterative methods. For example, 10-20 of 40-60 base overlapping oligonucleotides are assembled into a single 500 base subunit due to the need for overlapping ends, and twelve or more 500 base overlapping subunits are assembled into a single 5000 base synthetic gene. Each subunit of this process is typically cloned (i.e., ligated into a plasmid vector, transformed into a bacterium, expanded, and purified) and its DNA sequence is verified before proceeding to the next step. If the above gene synthesis process has low fidelity, either due to errors introduced by low quality of the initial oligonucleotide building blocks or during the enzymatic steps of subunit assembly, then increasing numbers of cloned isolates must be sequence verified to find a perfect clone to move forward in the process or an error-containing clone must have the error corrected using site directed mutagenesis.

Traditional methods for assembly have suffered from shortcomings of being unable to clone low complexity sequence motifs such as repeats, homopolymeric nucleotide runs, and high/low GC sequences. In addition, the ability to generate libraries of high sequence variation at defined sequences is even more problematic. Methods for overcoming these limitations have been developed that are based on the synthesis and incorporation of highly pure long single stranded oligonucleotides, such as Ultramers™ oligonucleotides (Integrated DNA Technologies, Inc.) into double stranded clonal/non-clonal PCR products (see gBlocks® gene block fragments from Integrated DNA Technologies, Inc.). Once fully assembled, the double stranded material can be subjected to error correction methodologies to improve the fidelity of the end product.

Libraries containing high sequence variation at defined sequences (see gBlocks® Gene Fragments Libraries from Integrated DNA Technologies, Inc.) consist of a specific sequence of DNA synthesized in the form of linear double stranded DNA. Libraries are designed to include variation within a single base to large region of sequence but limits the amount of variation present in each molecule of DNA. A common example is a hifi library consisting of the coding sequence of a variable chain of an antibody. The library may be constructed so that each codon within the chain is varied with an NNK sequence, but no single molecule contains more than one variation. This allows the researcher to explore variation over a large area of the sequence while limiting the variation to a number of sequences to be screened to $N^{32}$ variations, where N is the number of codons in the sequence. This type of library itself is not novel and is often described in the literature under a more general term of saturation mutagenesis, however the construction of this type of library is usually costly and very time consuming. It is also almost impossible to eliminate the background of wild type sequence from the final construct, increasing the amount of screening required to assess all possible variants.

The methods of the invention described herein provide high quality synthetic genes containing regions of high variability. Although derived from clonally purified wild type parent sequences, the recombination rate is such that the percent of the wild type sequence present in the final mixture is greatly diminished. These and other advantages of the invention, as well as additional inventive features, will be apparent from the description of the invention provided herein.

BRIEF SUMMARY OF THE INVENTION

The methods described here include the synthesis of long, double stranded nucleic acid sequences containing regions of low complexity, repeating elements, sequences traditionally difficult to assemble and clone, or variable regions containing mixed bases.

The invention uses clonally purified genes as the template for the construction of a library containing regions of sequence variability. The amplification of the library is such that only the sequences that have undergone recombination are amplified and not the original template sequence. Furthermore, it reduces the amount of intermediate products needed for library construction and the number of assemblies by an order of magnitude.

The invention pertains to two unique steps to reduce wild type carry over when constructing a library when using a cloned product as a template. The method involves cloning a template sequence, minus an amount of sequence from each terminal end. In one embodiment, the amount of sequence removed is consistent with the length and Tm balance needed as a priming region to perform PCR. Additional primers with the sequence of interest (this can include regions of degeneracy or known sequence) are designed to introduce a unique region via PCR.

The invention can be used to create a single unique construct or libraries of constructs with unique sequences from a cloned template without having wild type template carry over during the creation and assembly process.

The invention reduces the amount of wild type sequence carryover when using cloned product as the starting template from a library assembly process. It also limits the amount of starting material and intermediate products that need to be manufactured and QCed. Because the starting template is a cloned product the fidelity of the clone is very close to 100%. This allows a higher fidelity final product and the potential for a much longer product that could be assembled with oligos or gBlocks as the template.

The final DNA fragments or library can then be inserted into vectors, such as bacterial DNA plasmids, and clonally amplified through methods well-known in the art.

DETAILED DESCRIPTION OF THE INVENTION

Figure 1:
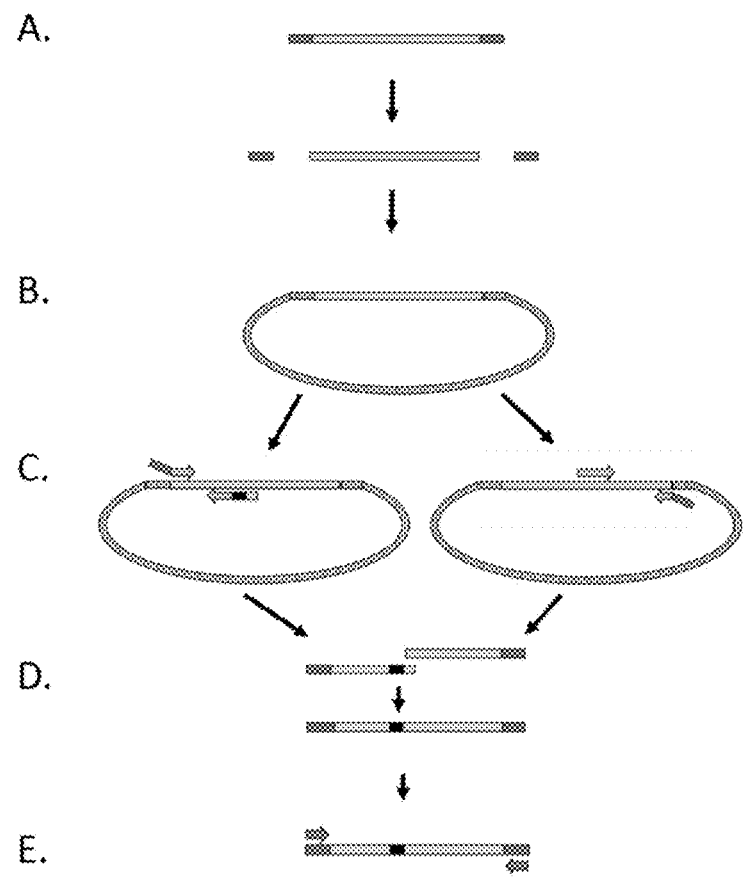
FIG. 1 is an illustration of one embodiment of the invention. (A) A synthetic gene is truncated at both of its terminal ends (dark gray). (B) The truncated gene (light gray) is then cloned into a vector. (C) Two PCR reactions are performed. The first reaction has a forward primer containing a sequence complementary to the 3' end of the cloned sequence and a 5' tail that serves to reintroduce the terminal upstream sequence that has been previously cleaved off, the reverse primer is complementary to a region within the cloned gene but with a variable region (black) in its center. The second reaction has a forward primer that anneals to a region within the cloned gene and a reverse primer complementary to the other end of the gene and with a 5' tail with the other cleaved terminal sequence. (D) The two PCR products produced are then ligated together either by PCR if they overlap, or blunt end ligation. (E) The newly assembled gBlock contains the variable region in the center as well as the two terminal regions that were cleaved off in the beginning. These two terminal regions then serve as targets for amplification primers. Since the cloned wild type template gene lacks these terminal regions, it is not amplified. Thus, only the recombinant genes are amplified.

Aspects of this invention relate to methods for the preparation of synthetic nucleic acid elements that may comprise genes or gene fragments. More specifically, the methods of the invention include methods of inserting variable sequences into clonally purified genes via PCR with primers containing degenerate, variable or repeat sequences. In one embodiment, a primer may include degenerate or mismatch bases within its central region to alter the sequence of synthetic gene. In another or further embodiment, primers that contain 5' tails introduce terminal regions not present in the wild type clone to be used in amplification of the recombinant genes only.

The term "oligonucleotide," as used herein, refers to polydeoxyribonucleotides (containing 2-deoxy-D-ribose), polyribonucleotides (containing D-ribose), and to any other type of polynucleotide which is an N glycoside of a purine or pyrimidine base. There is no intended distinction in length between the terms "nucleic acid", "oligonucleotide" and "polynucleotide", and these terms can be used interchangeably. These terms refer only to the primary structure of the molecule. Thus, these terms include double- and single-stranded DNA, as well as double- and single-stranded RNA. For use in the present invention, an oligonucleotide also can comprise nucleotide analogs in which the base, sugar or phosphate backbone is modified as well as non-purine or non-pyrimidine nucleotide analogs.

The term "primer", as used herein, refers to a short, single stranded oligonucleotide that serves as a starting point for DNA synthesis. It is required for PCR replication because the DNA polymerases used to catalyze this process can only add new nucleotides to an existing strand of DNA. Primers are, for the most part, complementary to the template strand to be replicated, yet they could contain regions of non-complementarity within the primer or at its 5' end. The term "bridging primer" refers to a primer that anneals to a central region within a wild type template. This primer is used to insert variable regions within the wild type to create recombinant sequences. The term "tailed primer" refers to a primer with two moieties; one on its 3' end which anneals to one of the ends of the cloned wild type template, and one on its 5' end that doesn't anneal and creates an overhang region. In this invention, tailed primers are used to add terminal sequences to the recombinant genes for use in subsequent PCR amplification.

The term "wild type", as used herein, refers to a parent nucleotide sequence that has not yet been altered via the recombination methods described here. The term "recombinant" refers to a sequence generated from the wild type sequence, but with a sequence alteration.

The term "synthetic gene" refers to a double stranded DNA fragment (of clonal or non-clonal origin), sometimes referred to as "gBlocks", gene sub-blocks or gene blocks. The synthesis of gBlocks is described in U.S. application Ser. No. 13/742,959 and is referenced herein in its entirety.

The term "base" as used herein includes purines, pyrimidines and non-natural bases and modifications well-known in the art. Purines include adenine, guanine and xanthine and modified purines such as 8-oxo-N6-methyladenine and 7-deazaxanthine. Pyrimidines include thymine, uracil and cytosine and their analogs such as 5-methylcytosine and 4,4-ethanocytosine. Non-natural bases include 5-fluorouracil, 5-bromouracil, 5-chlorouracil, 5-iodouracil, hypoxanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methyl ester, uracil-5-oxyacetic acid (v), 5-methyl-2-thiouracil, 3-(3-amino-3-N-2-carboxypropyl) uracil, (acp3)w, nitroindole, and 2,6-diaminopurine.

The term "base" is sometimes used interchangeably with "monomer", and in this context it refers to a single nucleic acid or oligomer unit in a nucleic acid chain.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence.

The oligonucleotides used in the inventive methods can be synthesized using any of the methods of enzymatic or chemical synthesis known in the art, although phosphoramidite chemistry is the most common. The oligonucleotides may be synthesized on solid supports such as controlled pore glass (CPG), polystyrene beads, or membranes composed of thermoplastic polymers that may contain CPG. Oligonucleotides can also be synthesized on arrays, on a parallel microscale using microfluidics (Tian et al., Mol. BioSyst., 5, 714-722 (2009)), or known technologies that offer combinations of both (see Jacobsen et al., U.S. Pat. App. No. 2011/0172127).

Synthesis on arrays or through microfluidics offers an advantage over conventional solid support synthesis by reducing costs through lower reagent use. The scale required for gene synthesis is low, so the scale of oligonucleotide product synthesized from arrays or through microfluidics is acceptable. However, the synthesized oligonucleotides are of lesser quality than when using solid support synthesis (See Tian infra.; see also Staehler et al., U.S. Pat. App. No. 2010/0216648). High fidelity oligonucleotides are required in some embodiments of the methods of the present invention, and therefore array or microfluidic oligonucleotide synthesis will not always be compatible.

In one embodiment of the present invention, the oligonucleotides that are used for gene synthesis methods are high-fidelity oligonucleotides (average coupling efficiency is greater than 99.2%, or more preferably 99.5%). High-fidelity oligonucleotides are available commercially up to 200 bases in length (see Ultramer® oligonucleotides from Integrated DNA Technologies, Inc.). Alternatively, the oligonucleotide is synthesized using low-CPG load solid supports that provide synthesis of high-fidelity oligonucleotides while reducing reagent use. Solid support membranes are used wherein the composition of CPG in the membranes is no more than 8% of the membrane by weight. Membranes known in the art are typically 20-50% (see for example, Ngo et al., U.S. Pat. No. 7,691,316). In a further embodiment, the composition of CPG in the membranes is no more than 5% of the membrane. The membranes offer scales as low as subnanomolar scales that are ideal for the amount of oligonucleotides used as the building blocks for gene synthesis. Less reagent amounts are necessary to perform synthesis using these novel membranes. The membranes can provide as low as 100-picomole scale synthesis or less.

Other methods are known in the art to produce high-fidelity oligonucleotides. Enzymatic synthesis or the replication of existing PCR products traditionally has lower error rates than chemical synthesis of oligonucleotides due to convergent consensus within the amplifying population. However, further optimization of the phosphoramidite chemistry can achieve even greater quality oligonucleotides, which improves any gene synthesis method. A great number of advances have been achieved in the traditional four-step phosphoramidite chemistry since it was first described in the 1980's (see for example, Sierzchala, et al. *J. Am. Cem. Soc.,* 125, 13427-13441 (2003) using peroxy anion deprotection; Hayakawa et al., U.S. Pat. No. 6,040,439 for alternative protecting groups; Azhayev et al, *Tetrahedron* 57, 4977-4986 (2001) for universal supports; Kozlov et al., *Nucleosides, Nucleotides, and Nucleic Acids,* 24 (5-7), 1037-1041 (2005) for improved synthesis of longer oligonucleotides through the use of large-pore CPG; and Damha et al., *NAR,* 18, 3813-3821 (1990) for improved derivitization).

Regardless of the type of synthesis, the resulting oligonucleotides may then form the smaller building blocks for longer oligonucleotides or gBlocks. As referenced earlier, the smaller oligonucleotides can be joined together using protocols known in the art, such as polymerase chain assembly (PCA), ligase chain reaction (LCR), and thermodynamically balanced inside-out synthesis (TBIO) (see Czar et al. Trends in Biotechnology, 27, 63-71 (2009)). In PCA oligonucleotides spanning the entire length of the desired longer product are annealed and extended in multiple cycles (typically about 55 cycles) to eventually achieve full-length product. LCR uses ligase enzyme to join two oligonucleotides that are both annealed to a third oligonucleotide. TBIO synthesis starts at the center of the desired product and is progressively extended in both directions by using overlapping oligonucleotides that are homologous to the forward strand at the 5' end of the gene and against the reverse strand at the 3' end of the gene.

Another method of synthesizing a larger synthetic gene or gBlock is to combine smaller oligonucleotides through top-strand PCR (TSP). In this method, a plurality of oligonucleotides span the entire length of a desired product and contain overlapping regions to the adjacent oligonucleotide (s). Amplification can be performed with universal forward and reverse primers, and through multiple cycles of amplification a full-length double stranded DNA product is formed. This product can then undergo optional error correction and further amplification that results in the desired synthetic gene (gBlock) end product.

In one method of TSP, the set of smaller oligonucleotides that will be combined to form the full-length desired product are between 40-200 bases long and overlap each other by at least about 15-20 bases. For practical purposes, the overlap region should be at a minimum long enough to ensure specific annealing of oligonucleotides and have a high enough melting temperature ($T_m$) to anneal at the reaction temperature employed. The overlap can extend to the point where a given oligonucleotide is completely overlapped by adjacent oligonucleotides. The amount of overlap does not seem to have any effect on the quality of the final product. The first and last oligonucleotide building block in the assembly should contain binding sites for forward and reverse amplification primers. In one embodiment, the terminal end sequence of the first and last oligonucleotide contain the same sequence of complementarity to allow for the use of universal primers.

Methods of mitigating synthesis errors are known in the art, and they optionally could be incorporated into methods of the present invention. The error correction methods include, but are not limited to, circularization methods wherein the properly assembled oligonucleotides are circularized while the other product remain linear and was enzymatically degraded (see Bang and Church, *Nat. Methods,* 5, 37-39 (2008)). The mismatches can be degraded using mismatch-cleaving endonucleases such as Surveyor® Nuclease. Another error correction method utilizes MutS protein that binds to mismatches, thereby allowing the desired product to be separated (see Carr, P. A. et al. *Nucleic Acids Res.* 32, e162 (2004)).

The degenerate bases are a random mixture of multiple bases (also known as "mixed bases"), and for the purposes of this application can also refer to non-standard bases or spacers such as propanediol. For example, the degenerate bases may be an N mixture (a mixture of A, C, G and T bases), a K mixture (G and T bases), or an S mixture (G and C bases). Examples of non-standard bases include universal bases such as 3-nitropyrrole or 5-nitroindole.

The degenerate bases can be added for the purpose of increasing or reducing the GC content, or to construct a mutation library. In one embodiment a particular region of interest in a sequence is targeted to determine the effects of alternate bases on the expression of the encoded product. Only a relatively small amount of randomers inserted in the bridging primer could produce a large mutant library. Each N base would result in 4 different products. Each additional N base added by the bridging primer would exponentially increase the library so that 2 N bases results in 16 combinations, 3 N bases results in 64, etc. By the time 18 N bases are inserted, the library contains over 68 billion different gene fragments. The cost of producing a library through the use of the methods of the invention is exponentially less expensive than through synthesizing each member of the library individually.

Standard PCR methods well-known in the art, following the general scheme in FIG. 1A, can be used to generate a double-stranded DNA fragment containing the bridge sequence between the adjacent gene block sequences. This end product double stranded DNA gene fragment or library can be treated as any other gene fragment described herein.

The gene blocks or libraries can then later be cloned through methods well-known in the art, such as isothermal assembly (e.g., Gibson et al. *Science,* 319, 1215-1220

(2008)); ligation-by-assembly or restriction cloning (e.g., Kodumal et al., *Proc. Natl. Acad. Sci. U.S.A.*, 101, 15573-15578 (2004) and Viallalobos et al., *BMC Bioinformatics*, 7, 285 (2006)); TOPO TA cloning (Invitrogen/Life Tech.); blunt-end cloning; and homologous recombination (e.g., Larionov et al., *Proc. Natl. Acad. Sci. U.S.A.*, 93, 491-496). The gene blocks can be cloned into many vectors known in the art, including but not limited to pUC57, pBluescriptII (Stratagene), pET27, Zero Blunt TOPO (Invitrogen), psi-CHECK-2, pIDTSMART (Integrated DNA Technologies, Inc.), and pGEM T (Promega).

The gene blocks or libraries can be used in a variety of applications, not limited to but including protein expression (recombinant antibodies, novel fusion proteins, codon optimized short proteins, functional peptides—catalytic, regulatory, binding domains), microRNA genes, template for in vitro transcription (IVT), shRNA expression cassettes, regulatory sequence cassettes, micro-array ready cDNA, gene variants and SNPs, DNA vaccines, standards for quantitative PCR and other assays, and functional genomics (mutant libraries and unrestricted point mutations for protein mutagenesis, and deletion mutants).

One embodiment of the invention, a creation of a library in which multiple bridging primers, each containing a degenerate region at successive positions, are used to form a double stranded DNA walking library, could be used in a number of applications. This type of library is useful for introducing one amino acid change at a time along the sequence of interest, while keeping the other amino acids constant. This could be a useful tool in homologous recombination with gene editing technologies such as CRISPR.

In one embodiment, the wild type synthetic gene sequence is truncated at both termini by removing sequence sufficient to design tm balanced primers (FIG. 1A). Additional sequence may be removed to facilitate optimal primer design. The truncated gene sequence is then cloned into a plasmid which is purified from a clonal population of bacteria using standard techniques for plasmid preparation (FIG. 1B).

Two different PCR reactions amplify the upstream and downstream regions of the cloned gene, respectively. In both reactions, tailed primers are designed to bind to one or the other truncated terminus of the gene sequence (FIG. 1C). These tailed primers contains a 5' tail consisting of the truncated sequence (FIG. 1C, dark grey). In one reaction (FIG. 1C, left), a bridging primer is used introduce a region of variation. This bridging primer contains a 3' binding site, a region of variation, and a 5'binding site. The second PCR reaction (FIG. 1C, right) is similar to the first, but amplifies the downstream part of the cloned gene.

The resulting amplicons contain one or more variations introduced by the bridging primer and the additional terminal sequence of the synthetic gene prior to truncation. These are then joined to form the complete recombinant synthetic gene (FIG. 1D).

Primers designed to amplify from the tails of the tailed primers produce the final product. Because the final primers hybridize to sequence not present in the original truncated gene sequence used as template, the amplification of sequence from the cloned template is eliminated (FIG. 1E).

Figure 2:
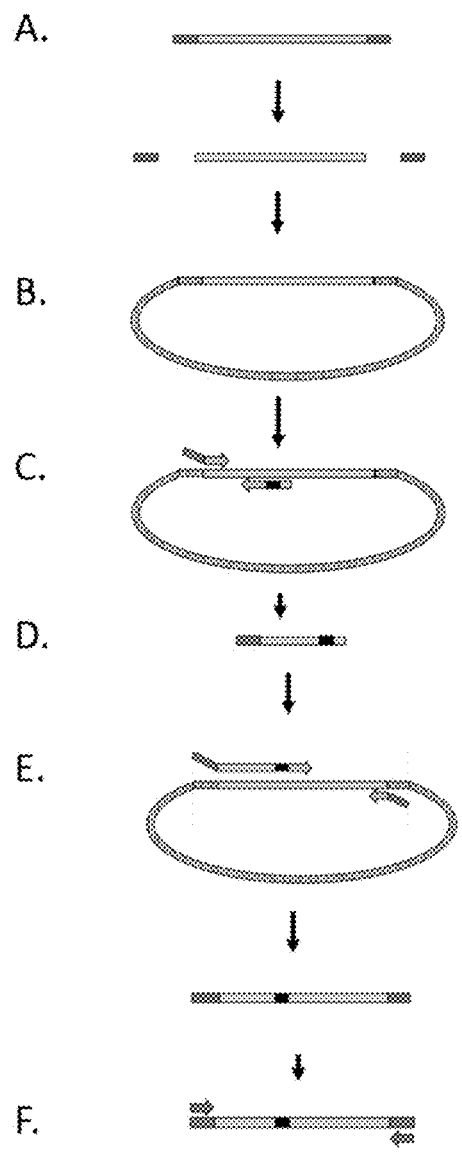
FIG. 2 is an illustration of a second embodiment of the invention. (A)-(C). As in first embodiment, the terminal ends of the wild type gene are cleaved off and the resulting product is then cloned into a vector. PCR is performed where a forward primer with a 5' tail serves to reintroduce the upstream sequence that has been previously cleaved off, and a reverse primer with a variable region within to gene. (D) The resulting product, which consists of the upstream region of the gene with the newly added terminal region (dark gray) and a variable region (black) is purified. (E) The purified product is then itself used as a forward primer in a second PCR reaction which amplifies the cloned gene. The reverse primer in this reaction has 5' tail with the other cleaved terminal sequence. The newly produced gene contains the variable region in the center as well as the two terminal regions that were cleaved off in the beginning. (F) These two terminal regions then serve as targets for amplification primers. Since the wild type gene lacks these terminal regions while in the vector, it is not amplified. Thus, only the recombinant genes are amplified.

In another embodiment, the wild type synthetic gene sequence is truncated at both termini by removing sequence sufficient to design tm balanced primers (FIG. 2A). Additional sequence may be removed to facilitate optimal primer design. The truncated gene sequence is then cloned into a plasmid which is purified from a clonal population of bacteria using standard techniques for plasmid preparation (FIG. 2B).

PCR1. A tailed primer is designed to bind to the truncated terminus of the Gene sequence (FIG. 2C). This tailed primer also contains a 5' tail consisting of the truncated sequence. The tailed primer is used along with one or more bridging primers in a PCR (FIG. 2C). Bridging primers include a 3' binding site, a region of variation, and a 5'binding site. The resulting amplicon contains one or more variations introduced by the bridging primer and the additional terminal sequence of the synthetic gene prior to truncation (FIG. 2D).

The amplicon for PCR1 is purified to remove any unincorporated primers from the reaction. In one embodiment, Agencourt AMPure XP magnetic beads (Beckman Coulter) can be used for this purpose.

The purified PCR1 product is used as a primer for PCR2 along with the other tailed terminal primer (FIG. 2E).

PCR2 Rescue. Primers designed to amplify from the tails of the tailed primers produce the final product. Because the final primers hybridize to sequence not present in the original truncated Gene sequence used as template, the amplification of sequence from the cloned template is eliminated (FIG. 2F).

In another embodiment, the template sequence is not truncated. Instead, tailed primers are used to add a terminal sequence or terminal sequences, and the newly tailed product will be the only product incorporated in further rounds of amplification where variable sequences are incorporated.

What is claimed is:

1. A method of constructing a DNA library from a clonally purified synthetic gene with decreased contamination with the wild type background, said method comprising selectively amplifying recombinant sequences, the method comprising:
    a) truncating a gene fragment by cleaving off terminal sequences from both ends;
    b) inserting the truncated gene into a cloning vector;
    c) amplifying the cloned gene out of the vector using
        i. tailed primers that serve to add back the cleaved terminal sequences and
        ii. bridging primers that serve to introduce new sequences within the gene fragment; and
    d) amplifying the resulting amplicon using primers that target the terminal sequences.

* * * * *